Figure 1:
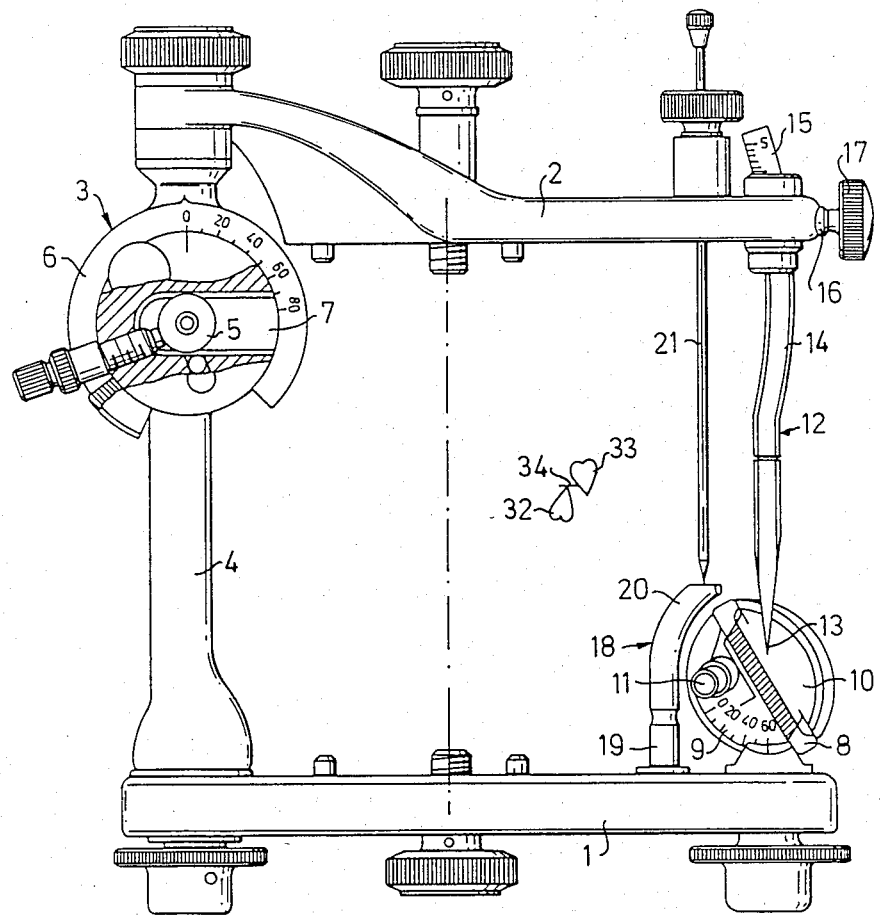

United States Patent [19]

Edwardson

[11] Patent Number: 4,505,674
[45] Date of Patent: Mar. 19, 1985

[54] ARTICULATOR FOR USE IN MAKING DENTURES OR PARTS THEREOF
[75] Inventor: Svante R. Edwardson, Solna, Sweden
[73] Assignee: AB Dentatus, Hagersten, Sweden
[21] Appl. No.: 510,899
[22] Filed: Jul. 5, 1983
[51] Int. Cl.³ .............................................. A61C 11/00
[52] U.S. Cl. .................................................... 433/59
[58] Field of Search ...................... 433/59, 64, 54, 55, 433/56

[56] References Cited

U.S. PATENT DOCUMENTS

| | | | |
|---|---|---|---|
| 1,670,311 | 5/1928 | Musante | 433/55 |
| 2,070,025 | 2/1937 | Phillips | 433/59 |
| 2,200,058 | 5/1940 | Chott | 433/59 |
| 2,371,795 | 3/1945 | Bodine | 433/59 |
| 2,432,624 | 12/1947 | Kinsley | 433/56 |
| 4,189,837 | 2/1980 | Stele | 433/59 |

FOREIGN PATENT DOCUMENTS 731864 6/1955 United Kingdom ................. 433/54
2066667 7/1981 United Kingdom ................. 433/64

Primary Examiner—John J. Wilson
Attorney, Agent, or Firm—Young & Thompson

[57] ABSTRACT

An articulator, for use in making dentures or parts thereof, comprises a lower and an upper principal member, which are interconnected by a condylar mechanism that allows relative movements between the principal members, a turnable incisal table attached to the lower principal member and an incisal pin lockably and vertically adjustably mounted in the upper principal member above the incisal table and having a tip pointing towards the table. The articulator has a separate freedom-in-centric guide table having an upper surface located outside the rotational center of the incisal table and an extra pin lockably and vertically adjustably mounted in the upper principal member above the freedom-in-centric guide table. The extra pin is mounted at the side of the incisal pin in a separate locking device and has a tip pointing towards the guide table.

8 Claims, 5 Drawing Figures

ARTICULATOR FOR USE IN MAKING DENTURES OR PARTS THEREOF

The present invention relates to an articulator, for use in making dentures or parts thereof, comprising a lower and an upper principal member which are interconnected by means of a condylar mechanism that allows relative movement between said principal members, and which lower principal member is substantially horizontal and has an adjustable incisal table at its end away from said condylar mechanism, and the upper principal member is substantially horizontal or can be set at small angle to a horizontal line, the angular movement normally being delimited by an incisal pin suspended from the upper principal member and supported by said incisal table. A mandibular cast is intended to be attached to the lower principal member and a maxillary cast is intended to be attached to the upper principal member.

Numerous types of articulators for simulating a patient's bite and jaw movements are found on the market. Many of them allow various kinds of adjustment from individual records in order to facilitate an accurate reproduction of the individual jaw movements.

In order to have a physical simulation of the protrusive movement by the jaws, the condylar mechanism has condylar balls mounted in condylar tracks so that they can be slidingly set as desired. In order to have the physical simulation of the physical guidance provided by the front teeth or incisors, the articulators have an incisal table on the lower principal member and an incisal pin mounted on the upper principal member having its tip resting on the incisal table. The incisal table is turnable and can be adjusted to be inclined at different angular positions.

In order to provide so-called freedom-in-centric, the incisal table in some articulators is provided with a so-called freedom-in-centric pin located in an oblong hole in the center of the incisal table. It is adjustable vertically and has a horizontal upper surface. The freedom-in-centric pin is not affected by the angular adjustment of the incisal table.

At work the incisal table is set to an angle representing the angle towards the horizontal of the tangent of the contact surface between the upper and the lower front teeth when they are in contact. This angle could be up to 60°. The freedom-in-centric pin and the incisal pin are raised in order to obtain a splint centric relation. Lateral guidance is achieved by lateral wings of the incisal table, which wings are settable at chosen angles to the surface of the incisal table.

A disadvantage of this conventional incisal table provided with the freedom-in-centric pin in the center is that it is difficult to set the freedom-in-centric pin in the right position because it is adjustable by turning a knob placed under the principal member and also because the incisal pin conceals the freedom-in-centric pin for the operator.

An object of the invention is therefore to provide a device which gives the same and better function as earlier and which makes it easy for an operator to set the instrument.

Another object of the invention is to provide a possibility for the operator to have a resilient reset function for the upper jaw or maxilla, when the cast is moving in a splint centric relation, i.e. when the guidance for the maxillary cast is horizontal and for protrusive movement, the maxillary cast is moved between the splint centric relation contact and the splint centric on tapping. Having this possibility, the operator can move the maxillary cast backwards and forwards and only feel the friction caused by the teeth in the cast, i.e. without feeling the friction caused by the pin sliding on the freedom-in-centric table.

Figure 2:
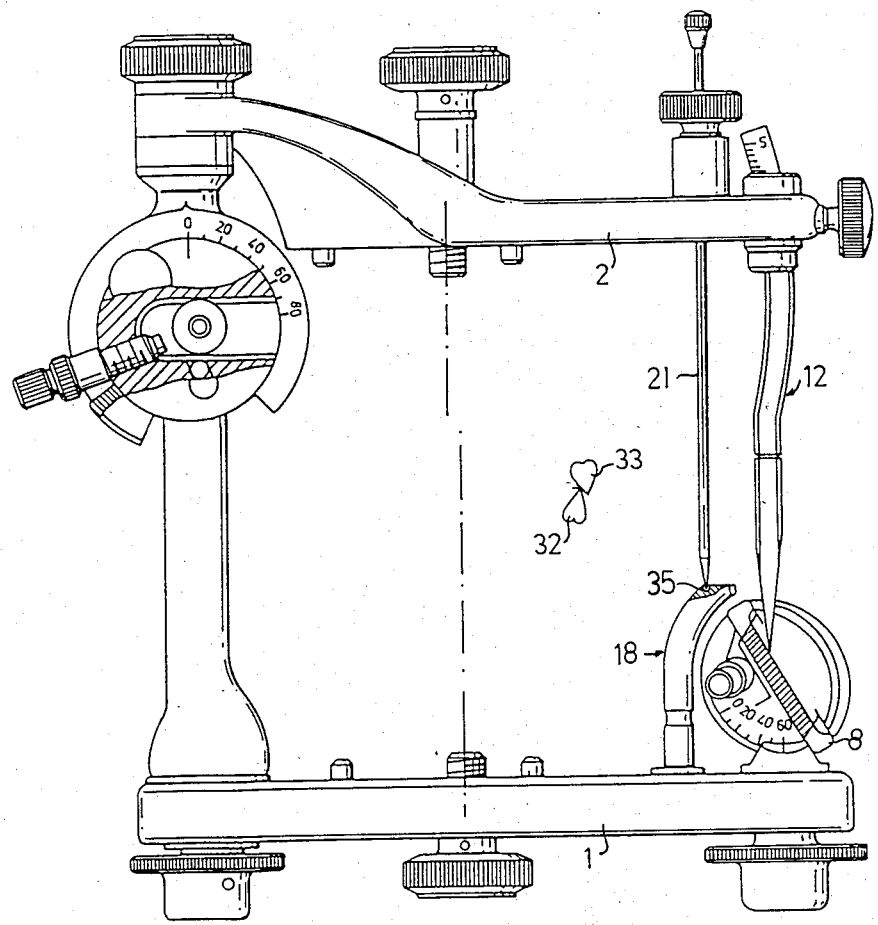
Figure 3:
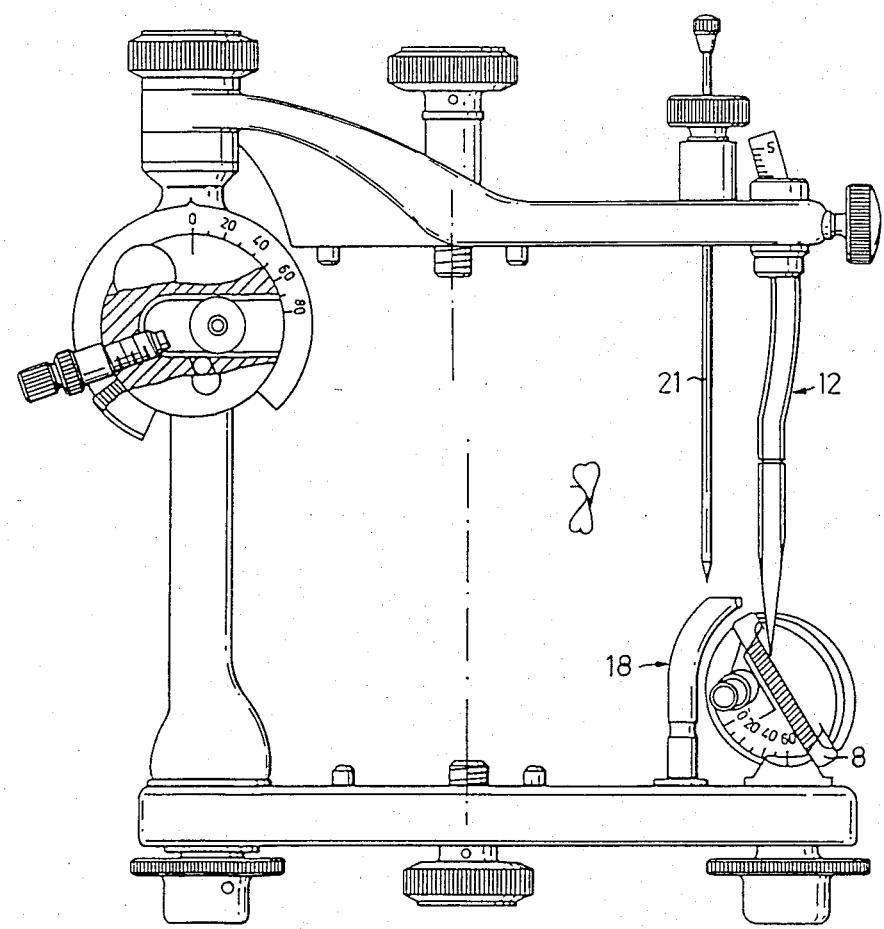
Figure 5:
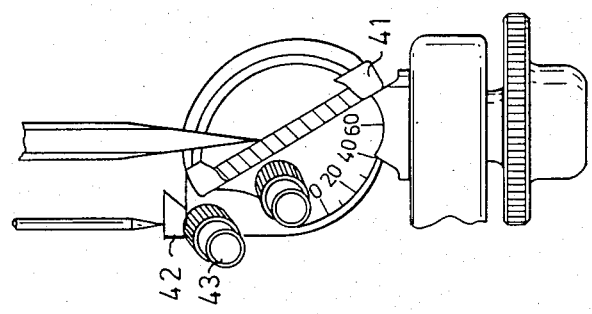
Figure 4:
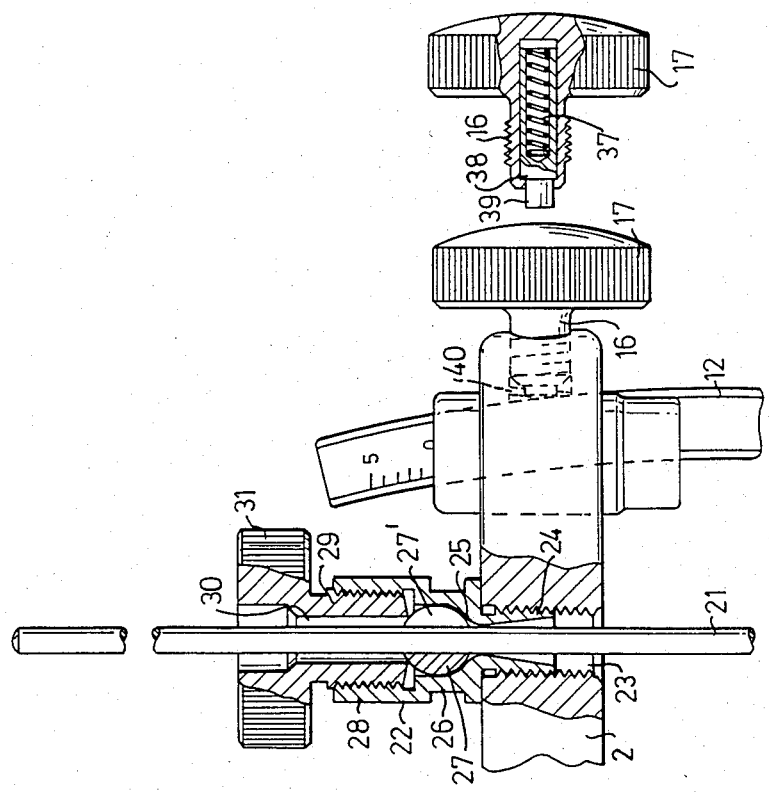

The invention will now be described with reference to the accompanying drawings, wherein:

FIGS. 1 to 3 are schematic views of an articulator provided with a first embodiment of the device according to the invention shown in different setting positions, FIG. 4 is a perspective view partly in section of a knob for adjustment operations of the incisal pin, and of the locking arrangement for the long-centric pin, and FIG. 5 is a schematic view of a guide table according to a second embodiment of the invention.

As can be seen from FIGS. 1 to 3, an articulator comprises a lower principal member 1 and an upper principal member 2. The principal members 1 and 2 are interconnected by a condylar mechanism 3 that allows relative movement between said principal members 1 and 2 simulating the movements of the jaw joint in a human being. In the arcon type of articulator shown in the Figures, the lower member 1 is provided with a support means 4 supporting two condylar balls 5, of which one is shown. The upper member 2 has two condylar track members 6, of which one is shown. A condylar ball 5 is resting in a track 7 in each member 6. The condylar mechanism is not a part of the invention and it is only shown as an example of a type which can be used. The invention is applicable also to articulators of condylar type having condylar track members supported by the lower principal member and condylar balls provided on the upper principal member.

An incisal table 8 is located in the front part of the lower principal member. The table 8 is of a kind commonly used in this technical field when no freedom-in-centric possibility is desired. It is rotatable around a horizontal axis perpendicular to the central axis of the instrument and can be set at chosen angular positions given by an angular scale 9. The incisal table is also provided with two lateral wings of which one 10 is shown in elevated position in FIG. 1. The wing turned towards the viewer is broken away in order not to conceal the center plane of the incisal table. The adjustments of the wings are made by set screws 11, one on each side of the incisal table.

An incisal pin 12 of a type common in the art is settably disposed in the upper principal member 2. The incisal pin 12 has a straight lower part with a tip having an edge 13 directed towards the table 8 and a curved upper part 14 having a scale 15. The setting of the incisal pin 12 is achieved with the aid of a locking screw 16 with a knob 17.

In accordance with the invention a freedom-in-centric guide table 18 is placed out from the center of the table 8. In the embodiment shown in the Figures, the guide table 18 is a pin having a lower straight part 19 which is rigidly fixed directly on the lower principal member 1, for instance screwed into a hole, and an upper curved part 20 having its curve center substantially on the axis of rotation of the incisal table 8. Preferably, the upper surface of the guide table 18 is horizontal.

A long vertical pin 21, called the long-centric pin, is mounted in the upper principal member 2 above the upper surface of the guide table 18. The long-centric pin 21 is adjustable in vertical direction and can also as desired be locked in a slightly inclined position. It is an advantage for the operator to have the pin 21 as near as possible to the incisal pin 12, i.e. as far as possible from the casts. Therefore, the section 20 of the table 18 is curved even though the function of the pin 21 and the table 18 would be the same with a straight table 18.

An embodiment of the locking device for the long-centric pin 21 is shown in FIG. 4. A housing 22 is screwed into a hole 23 in the upper principal member 2. The housing 22 has a central through-bore having different diameters in different sections in the housing. In a first lower section 24 screwed into the hole 23, the bore is tapered having its part with the smaller diameter turned upwards. The smaller diameter of the bore in the section 24 is slightly greater than the diameter of the pin 21.

The bore is also tapered in a second section 25 above the section 24 but has its wider part turned upwards. The section 26 above the section 25 has a constant diameter, which is the same as the upper diameter of the bore in the section 25 and which is substantially greater than the diameter of the pin 21. A steel ball 27, having practically the same diameter as the bore in the section 26, is placed in the bore in the sections 25 and 26. The ball 27 has a central hole in which the long-centric pin 21 is guided, and a slot 27' extending from the periphery to the hole in the same direction as the hole.

In the upper section 28 the bore has a diameter which is greater than the diameter of the bore in the section 26. The bore in the section 28 is threaded and a screw 29 having a central bore 30 having a diameter substantially greater than the diameter of the pin 21 is screwed into the bore in the section 28. The screw 29 is so long that it compresses the ball 27 to flexibly reduce the width of slot in order to firmly lock the adjusted position of the pin 21 when it is in an screwed-in position. The operator turns the screw 29 with a knob 31 at the top of the screw.

When the operator wishes to change the position of the pin 21, he loosens the screw 29 until it comes out of contact with the ball 27 and the ball comes out of its flexibly compressed state. Then the pin 21 can slide in the hole in the ball. The operator adjusts the pin to the desired vertical position and is also able to set it in a slightly inclined position pivoted around the center of the hole. Thereafter he screws in the screw 29 to lock the pin. The intention of having the pin 21 angularly settable will be described more in detail in connection with FIGS. 1 and 2.

FIGS. 1 to 3 show the articulator having the incisal pin 12, the incisal table 8 and the long-centric pin 21 already set in an adjusted position for work and show the articulator in different working positions. Only one front tooth 32 of the mandibular cast attached to the lower principal member 1 and one front tooth 33 of the maxillary cast attached to the upper principal member 2 are shown. The line 34 represents the desired path for the top of the tooth 32. The mandibular cast should be placed in the articulator in centric relation and having a splint-centric-relation contact. The pin 21 is resting on the table 18 and the edge of the incisal pin 12 is a short distance away from the inclined incisal table 8. The forward guidance for the upper member 2 is effected by the pin 21 and the guide table 18.

FIG. 1 shows a first long-centric guidance possibility in which the pin 21 slides on the table 18, and FIG. 2 shows a second long-centric guidance possibility in which the top of the pin 21 rests in a hole 35 in the upper surface of the table 18 near its back or its front edge. The pin 21 is resilient and the resilience of the pin makes the second guidance possibility possible. The operator uses the first guidance possibility when he wants to work with both a freedom-in-centric movement and an incisal guidance movement and can choose to have the second guidance possibility when he works only with freedom-in-centric movements. The two guidance possibilities are provided by setting the pin 21 in different inclined positions.

FIG. 3 shows the articulator in an incisal guidance movement position, in which the edge 13 of the incisal pin 12 has slided up on the incisal table 8 and the long-centric pin 21 is lifted up from contact with the guide table 8.

A particular kind of locking device 16,17 for the incisal pin 12 is shown in FIG. 4. It is an advantage for the articulator according to the invention to have the incisal pin 12 vertically adjustable in such a way that it can be moved vertically without being pivoted, because this opportunity makes it easier for the operator to make the correct setting of the instrument. For this reason, the locking device includes a set screw 16,17 having a compression spring 37 located in a central axial bore 38 with one open end at the end of the screw. The spring 37 is shorter than the bore 38, which has a narrow section at its outer end, in which a short plug 39 is placed slidable with friction. When the plug 39 is inserted in the bore 38 in contact with the end of the spring, a part of it projects out from the end of the screw. The screw is screwed into a horizontal bore 40 in the member 2 and opening into the guide slot or bore for the pin 12. In the locking position for the pin, the screw has its top firmly resting on the pin 13 and the plug 39 inserted against the action of the spring 37 (not shown). At adjustment of the position of the pin 12 the operator loosens the screw 36 to such an extent that its end comes out of contact with the pin but the end of the plug 39 is still resting on and pressed against the pin 12 by the spring 37.

The freedom-in-centric guide table need not necessarily be attached to the lower principal member 1. The guide table 42 can also be positioned on the side of the incisal table 41 as is shown in FIG. 5. The guide table 42 is turnable with a knob 43 to a horizontal position.

Although preferred embodiments of the present invention have been illustrated herein, it is to be understood that various changes and modifications may be made in the construction and arrangement of elements without departing from the spirit and scope of the invention is defined.

What I claim is:

1. An articulator, for use in making dentures or parts thereof, comprising a lower and an upper principal member which are interconnected by means of a condylar mechanism that allows relative movements between said principal members, a turntable incisal table having a rotational center and being attached to said lower principal member on a virtual center line dividing said principal member into two mirror-invertedly similar parts, an incisal pin lockably and vertically adjustably mounted in said upper principal member above said incisal table and having a tip pointing towards the table, a freedom-in-centric guide table having an upper surface located with its center in a vertical plane through said virtual center line and located outside said rotational center of said incisal table, and an extra pin lockably and vertically adjustably mounted in a separate locking device in said upper principal member above said freedom-in-centric guide table and having a tip pointing towards said guide table.

2. An articulator as claimed in claim 1, wherein said freedom-in-centric table is attached to said lower principal member beside said incisal table.

3. An articulator as claimed in claim 2, wherein said freedom-in-centric guide table has a curved upper part having its center of curvature substantially located at said rotational center of said incisal table.

4. An articulator as claimed in claim 1, wherein said guide table is mounted on said incisal table.

5. An articulator as claimed in claim 1, wherein said locking device for said extra pin is adjustable for setting said extra pin in an arbitrary angular position for said guide table.

6. An articulator as claimed in claim 1, wherein said upper table of said guide table is provided with a setting hole for said extra pin near one of its edges.

7. An articulator as claimed in claim 1, including a locking device for vertical setting of the incisal pin, said locking device comprising a set screw having a compression spring disposed in a central axial bore with one open end, having inserted therein a compression spring and a plug slidable with friction against a portion of the bore and biased by said spring into contact with said incisal pin when the set screw is screwed into said upper principal member into a horizontal threaded bore which opens into a guide slot for said incisal pin, in order to exert variable holding pressure on the incisal pin by turning said set screw.

8. An articulator as claimed in claim 1, including a locking device for said extra pin providing the possibility for setting the pin both longitudinally and in an arbitrary angular position, including a flexible ball having a central through-hole with reducible diameter at compression in which said pin is located, a housing having a through-bore in which said ball and said pin are disposed and which has a varying diameter having its smallest part direclty under the ball and having such dimensions that the pin can be set up to a predetermined maximum angle to the vertical, and means for compressing the ball at locking.

* * * * *